(12) United States Patent
Wu (10) Patent No.: US 10,555,836 B2
(45) Date of Patent: Feb. 11, 2020

(54) WELDING HELMET HAVING A HUD-TYPE AUTO-DARKENING FILTER

(71) Applicant: Tecmen Electronics Co., Ltd., Nanjing (CN)

(72) Inventor: Ziqian Wu, Nanjing (CN)

(73) Assignee: Tecmen Electronics Co., Ltd., Nanjing (CN)

( * ) Notice: Subject to any disclaimer, the term of this patent is extended or adjusted under 35 U.S.C. 154(b) by 142 days.

(21) Appl. No.: 15/507,686

(22) PCT Filed: Sep. 1, 2015

(86) PCT No.: PCT/CN2015/088740
§ 371 (c)(1),
(2) Date: Feb. 28, 2017

(87) PCT Pub. No.: WO2016/037539
PCT Pub. Date: Mar. 17, 2016

(65) Prior Publication Data
US 2017/0258639 A1    Sep. 14, 2017

(30) Foreign Application Priority Data
Sep. 9, 2014  (CN) .......................... 2014 1 0456014

(51) Int. Cl.
*A61F 9/06*          (2006.01)
*G02B 27/01*        (2006.01)
(Continued)

(52) U.S. Cl.
CPC ................ *A61F 9/067* (2013.01); *A61F 9/06* (2013.01); *G02B 27/0172* (2013.01);
(Continued)

(58) Field of Classification Search
CPC .. G02B 27/0172; G02B 27/01; G02B 27/017; G02B 27/0176; G02B 27/226;
(Continued)

(56) References Cited

U.S. PATENT DOCUMENTS 5,266,930 A * 11/1993 Ichikawa ............... A42B 3/042
345/8
5,856,811 A    1/1999 Shih et al.
(Continued)

FOREIGN PATENT DOCUMENTS

CN      1526364 A     9/2004
CN    101744683 A     6/2010
(Continued)

OTHER PUBLICATIONS

Miller Electric Mfg. Co., Auto-Darkening Helmets, Sep. 2013, p. 4.*
(Continued)

*Primary Examiner* — Clinton T Ostrup
*Assistant Examiner* — Patrick J. Lynch (57) ABSTRACT

A welding helmet includes a helmet housing; a headband structure for securing the helmet housing; a Head Up Display (HUD)-type auto-darkening filter secured in the helmet housing; and a light-permeable protective sheet installed in front of the HUD-type auto-darkening filter in the helmet housing, wherein the HUD-type auto-darkening filter comprises a head-up display which is used to reveal operating parameters of the auto-darkening filter, and the head-up display is arranged between a body of the auto-darkening filter and the protective sheet such that when the auto-darkening filter is in a transparent state the luminously revealed operating parameter of the auto-darkening filter can be imaged via the protective sheet into the eyes of an operator who wears the welding helmet.

17 Claims, 6 Drawing Sheets

(51) Int. Cl.
*G02F 1/13* (2006.01)
*A42B 3/22* (2006.01)
(52) U.S. Cl.
CPC ............ *G02B 27/0176* (2013.01); *G02F 1/13* (2013.01); *A42B 3/225* (2013.01)
(58) Field of Classification Search
CPC .. A61F 9/067; A61F 9/06; A61F 9/065; A61F 9/022; A61F 9/023; B23K 9/322; B23K 9/095; B23K 9/0953; B23K 9/0956; B23K 37/006; A42B 3/225; A42B 3/226; A41D 13/1184
USPC ............ 2/8.2, 8.3, 8.8; 349/11, 14; 359/601; 351/44; 345/7, 8
See application file for complete search history.

(56) References Cited

U.S. PATENT DOCUMENTS

| | | | |
|---|---|---|---|
| 5,959,705 A * | 9/1999 | Fergason | B23K 9/32 2/8.8 |
| 6,242,711 B1 | 6/2001 | Cooper | |
| 6,947,013 B2 * | 9/2005 | D'Achard Van Enschut | G02B 27/0101 345/6 |
| 2004/0131498 A1 | 7/2004 | Kuutti | |
| 2005/0017152 A1 | 1/2005 | Fergason | |
| 2007/0097277 A1* | 5/2007 | Hong | G02B 3/14 349/11 |
| 2008/0060102 A1* | 3/2008 | Matthews | A61F 9/061 2/8.2 |
| 2008/0158502 A1* | 7/2008 | Becker | A61F 9/067 351/44 |
| 2009/0276930 A1 | 11/2009 | Becker et al. | |
| 2010/0090997 A1 | 4/2010 | Huh | |
| 2010/0132086 A1 | 6/2010 | Huh | |
| 2011/0010815 A1 | 1/2011 | Huh | |
| 2011/0083241 A1 | 4/2011 | Cole | |
| 2011/0179541 A1 | 7/2011 | Wright | |
| 2013/0081190 A1 | 4/2013 | Wu | |
| 2013/0242110 A1* | 9/2013 | Terre | H04N 5/2251 348/164 |
| 2014/0043689 A1* | 2/2014 | Mason | G02B 27/0101 359/630 |
| 2014/0210987 A1 | 7/2014 | Adkins | |
| 2015/0209887 A1* | 7/2015 | DeLisio | B23K 9/0953 219/130.01 |
| 2015/0370074 A1* | 12/2015 | McDowall | G02B 27/0172 349/11 |
| 2016/0022496 A1* | 1/2016 | DeKeuster | G02F 1/13306 349/14 |

FOREIGN PATENT DOCUMENTS

| | | |
|---|---|---|
| CN | 101853639 A | 10/2010 |
| CN | 101953733 A | 1/2011 |
| CN | 102014819 A | 4/2011 |
| CN | 102573720 A | 7/2012 |
| CN | 103620478 A | 3/2014 |
| CN | 103826580 A | 5/2014 |
| CN | 204050009 U | 12/2014 |
| JP | H07-277293 A | 10/1999 |
| WO | 2005009309 A1 | 2/2005 |
| WO | 2008151393 A1 | 12/2008 |

OTHER PUBLICATIONS

State Intellectual Property Office of the P.R. China, International Search Report in International Application No. PCT/CN2015/088740 (dated Nov. 9, 2015).
The State Intellectual Property Office of People's Republic of China First Office Action dated Dec. 25, 2018 regarding Application No. 201410456014.4, 17 pages.
Office Action dated May 17, 2019 in connection with Australian Patent Application No. 2015315999, 3 pages.

* cited by examiner

WELDING HELMET HAVING A HUD-TYPE AUTO-DARKENING FILTER

CROSS-REFERENCE TO RELATED APPLICATIONS

This patent application is the U.S. national phase of International Patent Application No. PCT/CN2015/088740, filed Sep. 1, 2015, which claims the benefit of Chinese Patent Application No. 201410456014.4, filed on Sep. 9, 2014, which are incorporated by reference in their entireties herein.

FIELD

The present application generally relates to a welding helmet having a Head Up Display (HUD)-type auto-darkening filter.

BACKGROUND

In order to prevent an operator from being damaged by spattering matters and various harmful rays caused by welding-arc ignition, the operator usually wears a welding helmet on his/her head during a welding operation. In a conventional welding helmet, a light filter is an important component for protecting the operator's eyes from the harmful rays. Usually, the operator should first observe the position where the welding-arc ignition will occur. Then, the operator wears the conventional welding helmet on his/her head to carry out a blind operation. This kind of blind operation may lead to much inconvenience on welding sites.

For this reason, an auto-darkening welding helmet has been developed in recent years. The auto-darkening welding helmet is generally equipped with an auto-darkening filter. The auto-darkening filter can work mainly because it is provided with a liquid crystal panel. The liquid crystal panel is transparent before the welding-arc ignition. The liquid crystal panel becomes opaque at the moment of the welding-arc ignition starting, so as to protect the operator's eyes. The auto-darkening welding helmet is usually provided with an adjustment knob or button. Therefore, before wearing the welding helmet, the operator has to hold it in hand to set operating parameters, such as SENSITIVITY, delay time, shade, and weld mode or the like, of the auto-darkening filter. After the setting, the operator can wear the welding helmet on his/her head to carry out the welding operation. In case that the operating parameters must be adjusted repeatedly on some welding sites (for example to alter the weld mode or SENSITIVITY), repeatedly taking off/wearing the helmet will extremely consume the operator's energy, which may negatively affect the quality of welding.

In the course of taking off the helmet, setting the parameters and wearing the helmet again, the operator's eyes have to make constant self-regulation to adapt to bright or dark environmental change. Individual operators may even feel discomfort such that their welding work may be affected. In severer cases their eyes may be permanently damaged.

SUMMARY

It is an object of the present application to propose an improved auto-darkening welding helmet such that the operator can set the operating parameters of the auto-darkening filter without repeatedly taking off/wearing the helmet. Any discomfort of the operator caused by his/her eyes' continuous self-adjustment to bright or dark environmental change can be relieved. Further, the operator can always wear said proposed helmet on his/her head and at the same time set the various operating parameters so as to facilitate his/her welding work.

According to the present application, a welding helmet is provided, which comprises:
  a helmet housing;
  a headband structure for securing the helmet housing;
  a HUD-type auto-darkening filter secured in the helmet housing; and
  a light-permeable protective sheet installed in the helmet housing in front of the HUD-type auto-darkening filter,
  wherein the HUD-type auto-darkening filter comprises a head-up display which is used to reveal operating parameters of the auto-darkening filter, and the head-up display is arranged between a body of the auto-darkening filter and the protective sheet such that when the auto-darkening filter is in a transparent state the luminously revealed operating parameter of the auto-darkening filter can be imaged via the protective sheet into the eyes of an operator who wears the welding helmet.

Optionally, the protective sheet is spaced from the body of the auto-darkening filter in by a distance such that a virtual image of the luminously revealed operating parameter of the auto-darkening filter generated via the protective sheet can be watched by the operator's eyes.

Optionally, each operating parameter can be luminously revealed on the head-up display in a reversed manner.

Optionally, the head-up display is arranged obliquely relative to the protective sheet in the helmet housing.

Optionally, the head-up display is arranged at the bottom of the body of the auto-darkening filter in the helmet housing.

Optionally, the head-up display comprises a monochromatic or colour display screen.

Optionally, an adjustment knob is installed on the helmet housing of the welding helmet and is connected to the auto-darkening filter such that it can be used to adjust the operating parameters.

Optionally, adjustment of the operating parameters comprises adjustment of SHADE, which can be adjusted between 9 and 13 levels; adjustment of SENSITIVITY, which can be adjusted between 0 and 10 levels; adjustment of DELAY TIME, which can be adjusted between 0 and 10 levels; adjustment of welding mode, which can be switched between WELD, GRIND and CUTTING.

Optionally, the protective sheet is a transparent or semi-transparent protective sheet, especially a dark colored protective sheet.

Optionally, the protective sheet is detachably installed in the helmet housing.

The inventive welding helmet enables the operator to directly set the relevant operating parameters with the helmet being worn on his/her head, such that the operator's welding work is facilitated and his/her discomfort caused by the eyes' constant self-regulation to bright or dark environmental change can be relieved, and thus the operator's work efficiency can be enhanced. Further, the inventive welding helmet enables the operator to accomplish his/her welding work especially in a dark environment because the image generated via the head-up display can be much clearer.

BRIEF DESCRIPTION OF THE DRAWINGS

The foregoing and other aspects of the present application will be well understood by the following description in combination with the attached drawings. It should be noted that the drawings are illustrated in different scales for clarity. However, then cannot be deemed to affect understanding to the present application. In the drawings.

DETAILED DESCRIPTION

In the drawings of the present application, those features having the same configuration or having a similar function are represented by the same reference numerals.

Figure 1:
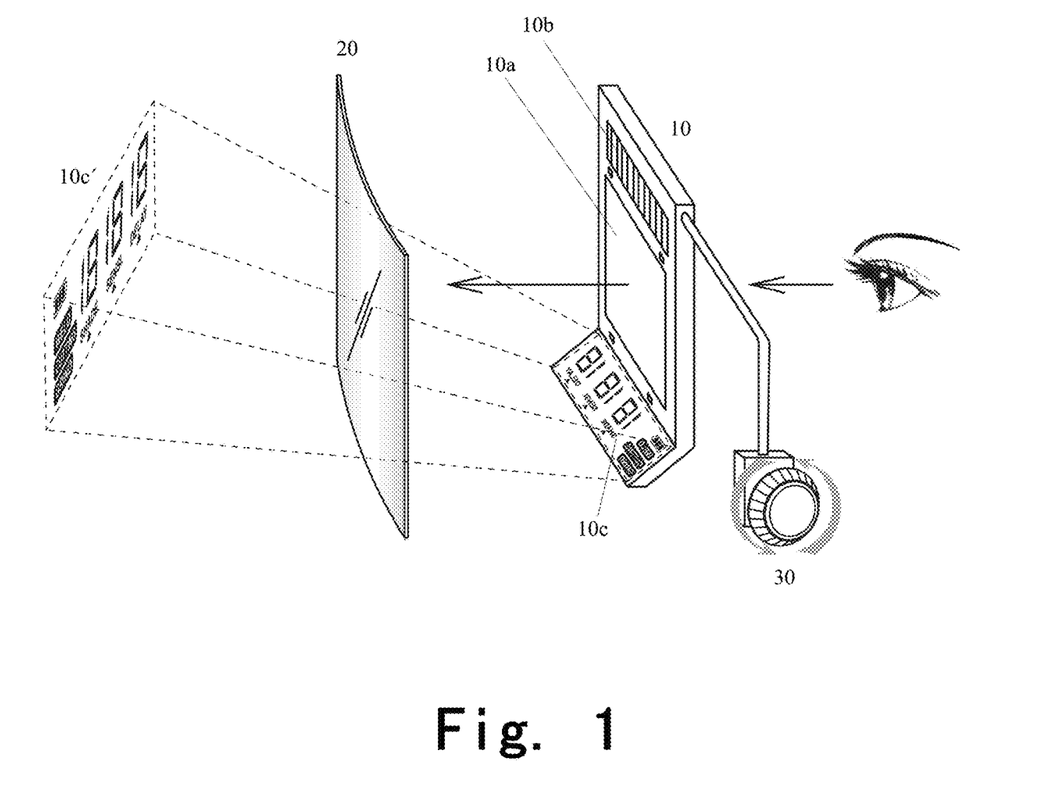
FIG. 1 is a view schematically illustrating the basic principle of a HUD-type auto-darkening filter according to the present application.

With a HUD-type auto-darkening filter according to the present application, it is unnecessary for an operator to take off a helmet already worn on his/her head when he/she intends to set operating parameters of the auto-darkening filter. As shown in FIG. 1, the auto-darkening filter 10 comprises a liquid crystal filter lens module 10a, a solar battery module 10b, and a head-up display 10c.

The liquid crystal filter lens module 10a and the solar battery module 10b are arranged on a body of the auto-darkening filter 10, and the head-up display 10c is arranged obliquely at the bottom of the body of the auto-darkening filter 10. The head-up display 10c can be a liquid crystal display on which all operating parameters relating to the auto-darkening filter 10 can be revealed timely.

It is noted that except for the head-up display 10c and its relevant contents cited below, the basic principle of the auto-darkening filter 10 is similar to those available on the market. Therefore, the basic principle of the auto-darkening filter 10 won't be explained here.

A control knob 30 is coupled to the auto-darkening filter 10 via a control cable and is used to adjust the operating parameters of the auto-darkening filter. Here, the adjustable operating parameters comprise SHADE, which can be adjusted between 9 and 13 levels; SENSITIVITY, which can be adjusted between 0 and 10 levels; DELAY TIME, which can be can be adjusted between 0 and 10 levels; and operation modes such as WELD, GRIND and CUTTING. Each of these operating parameters can be reversely displayed on the head-up display 10c.

It should be noted that in the context of the present application, for each character or letter or number to be displayed, the term "reverse" means that the character or letter or number displayed on the head-up display 10c is upside-down and left-right mirrored. Further, the head-up display 10c can comprise a monochromatic or colour liquid crystal screen or can be any other suitable display screen known by a person skilled in the art.

Figure 2:
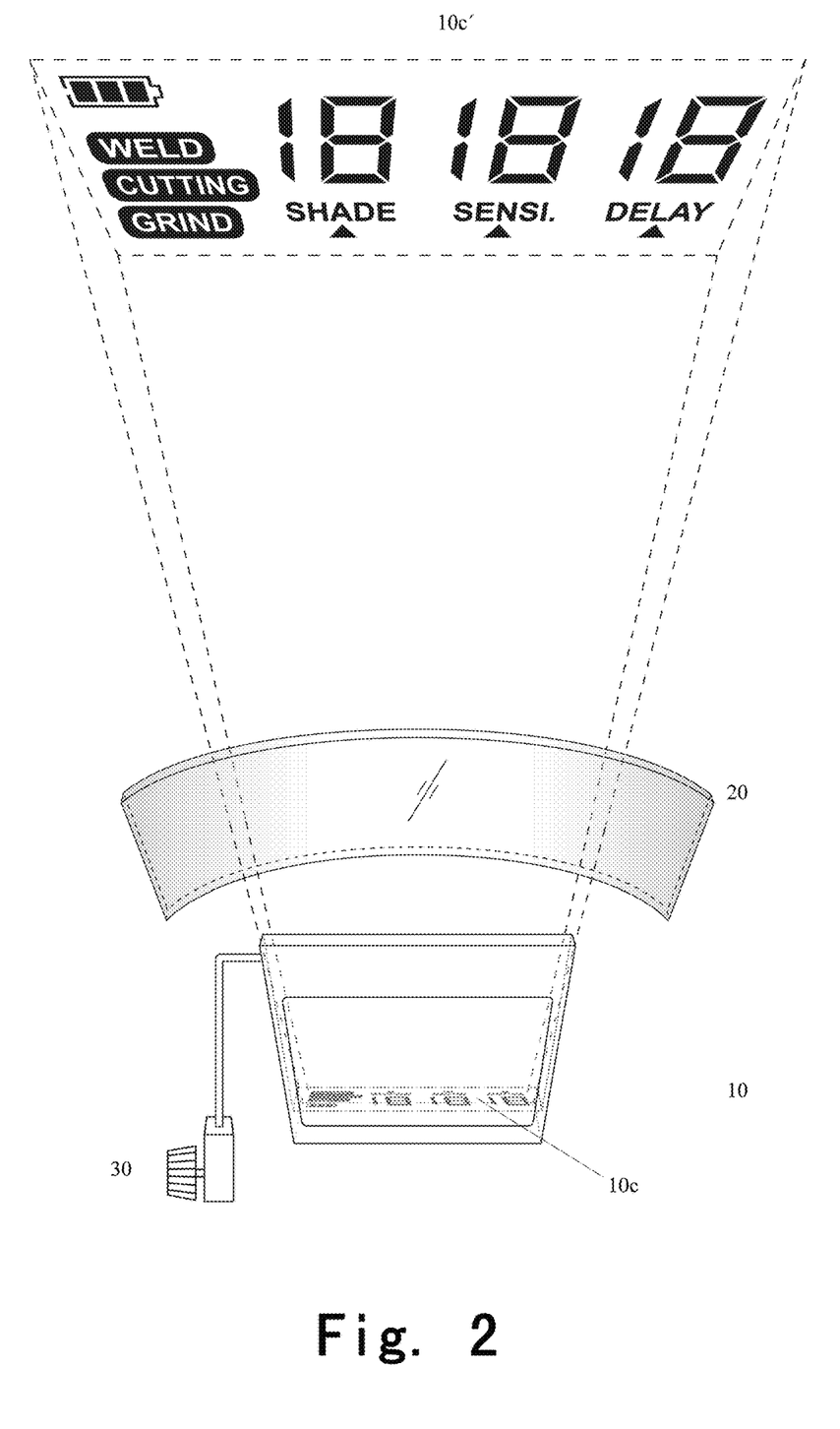
FIG. 2 is an enlarged top view schematically illustrating the HUD-type auto-darkening filter shown in FIG. 1.

A glass sheet 20 is arranged in front of the auto-darkening filter 10. The glass sheet 20 is light-permeable, especially transparent such that the main function of the auto-darkening filter 10 will not be negatively affected and the auto-darkening filter 10 is additionally protected from spattering matters caused by a welding operation. A luminous side of the head-up display 10c at the bottom of the auto-darkening filter 10 is arranged obliquely towards the glass sheet 20 such that light ray is emitted upwards and obliquely when the head-up display 10c is activated. One part of the emitted light ray transmits through the glass sheet 20 and the other part is reflected by the glass sheet 20 into one's eyes, such that as shown in FIG. 2, it seems that an enlarged positive virtual image of an operating parameter is provided at a given distance in front of the glass sheet 20 for the eyes. In this way, it is convenient for the operator to observe all the relevant operating parameters of the auto-darkening filter 10 without taking off the helmet.

Figure 3:
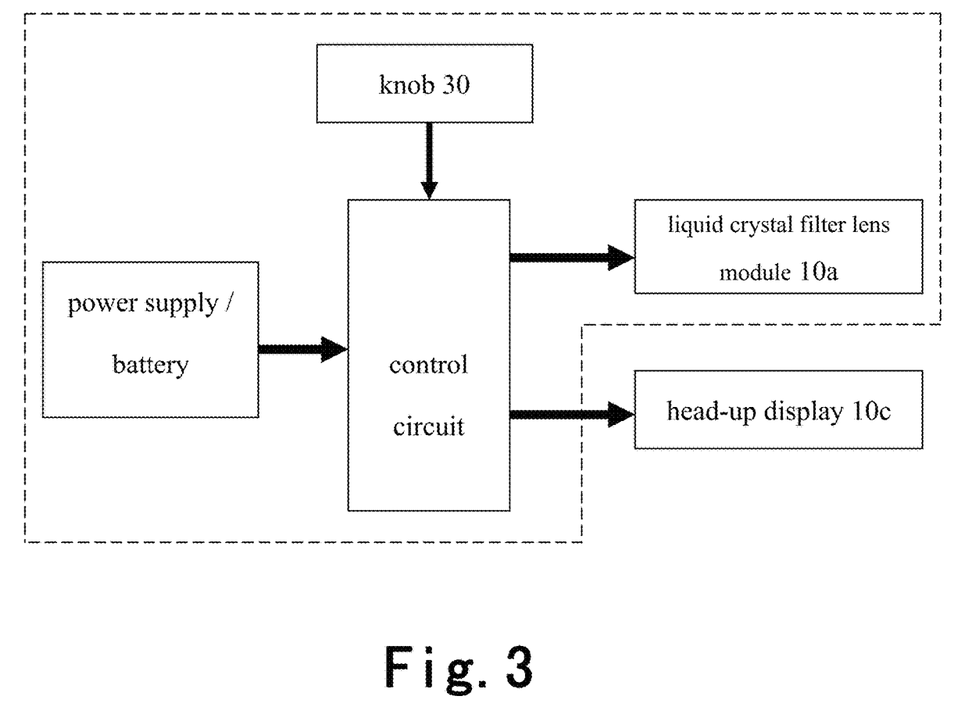
FIG. 3 is a basic control block diagram schematically illustrating the HUD-type auto-darkening filter.

FIG. 3 is a simplified control block diagram schematically illustrating the HUD-type auto-darkening filter. As shown in FIG. 3, a power supply/battery is connected to the liquid crystal filter lens module 10a via a control circuit, and the knob 30 is also connected to the liquid crystal filter lens module 10a via the control circuit such that the operating parameters of the auto-darkening filter 10 can be adjusted by the knob 30. It is appreciated that the battery, the control circuit, the liquid crystal filter lens module 10a, and the knob 30 (which are enclosed by a dashed box in FIG. 3) can be designed in a way similar to an auto-darkening filter known in the prior art. According to the present application, because the head-up display 10c is connected to the control circuit, it can be used to control the head-up display 10c to reversely reveal respective operating parameters when the operator wants to adjust them. Furthermore, the electrical quantity of the battery can be real-timely revealed on the head-up display 10c. From this point, the HUD-type auto-darkening filter according to the present application can be obtained by making a simple renovation on the basis of the known auto-darkening filter without greatly increasing manufacturing costs.

Further, the glass sheet 20 can be a transparent polymethyl methacrylate (PMMA) glass sheet or an ordinary glass sheet. In order to increase its reflectance, the glass sheet 20 can be affixed with a reflective film, for instance a reflective film commonly used in a car. Even in an alternative embodiment, the glass sheet 20 can be made as a dark and transparent glass sheet so as to provide a much clearer and enlarged positive virtual image under bright environmental condition. The glass sheet 20 can be even a transparent sheet used to protect the darkening filter of the known auto-darkening welding helmet. Further, although the head-up display 10c is shown in FIG. 2 to be obliquely arranged at the bottom of the liquid crystal filter lens module 10a, the head-up display is not limited to the shown arrangement manner. In an alternative embodiment, the head-up display 10c can be arranged obliquely aside the liquid crystal filter lens module 10a towards the glass sheet 20. That is to say, the head-up display 10c can be arranged at any suitable position where the light ray emitted from the head-up display 10c can project onto the glass sheet 20.

Figure 4:
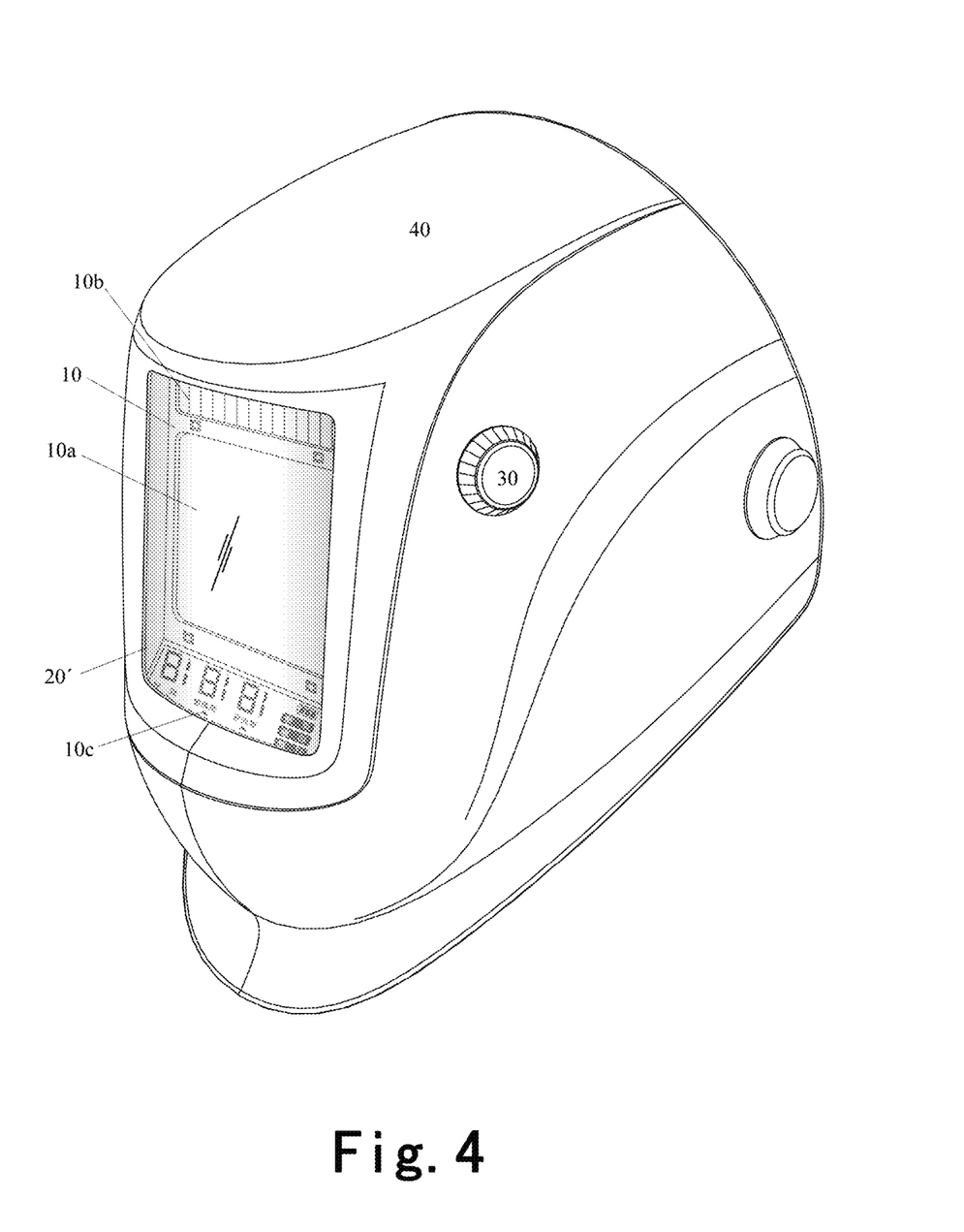
FIG. 4 is a perspective view schematically illustrating one embodiment of a welding helmet equipped with the HUD-type auto-darkening filter according to the present application.
Figure 5:
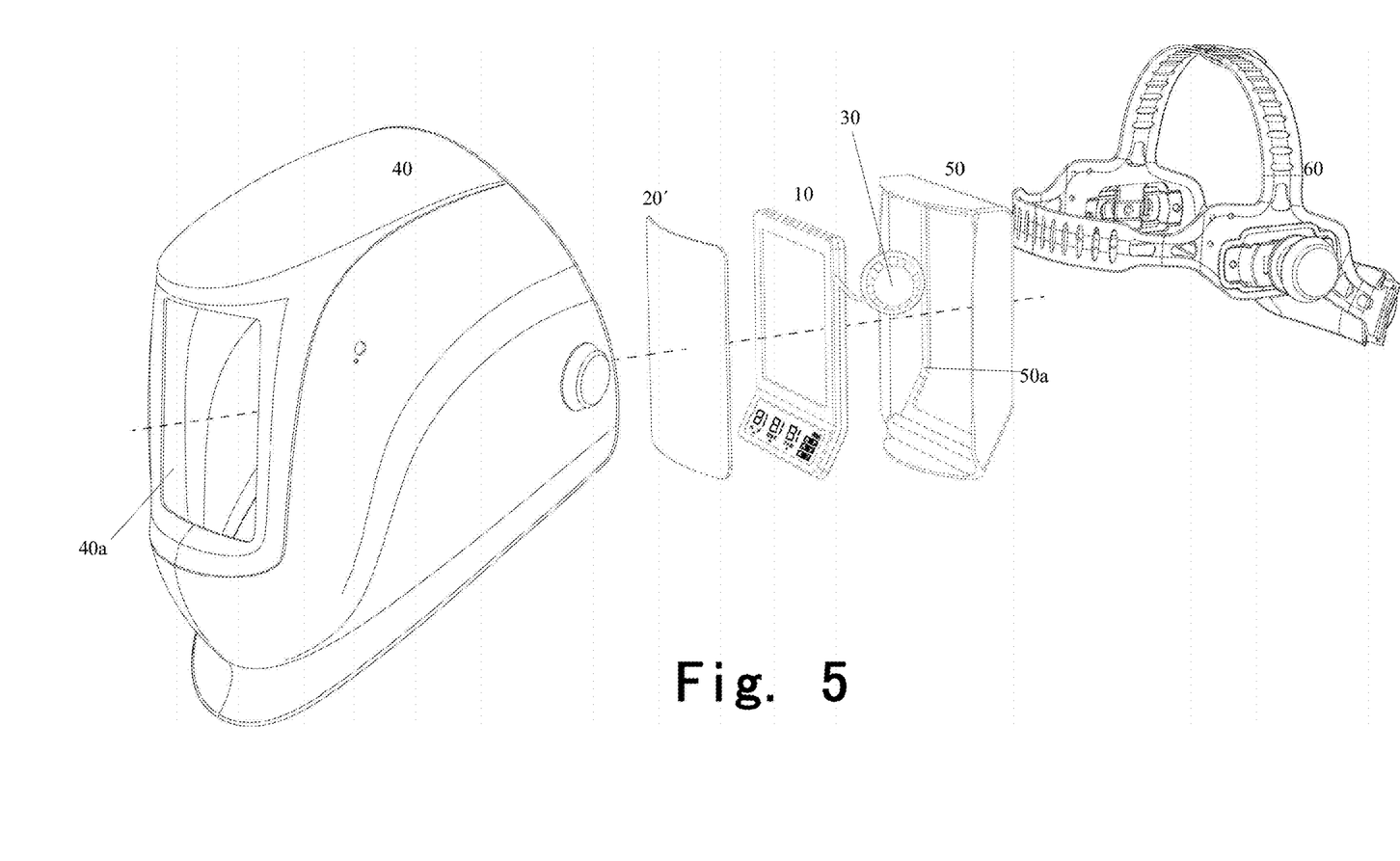
FIG. 5 is an exploded view schematically illustrating parts of the welding helmet shown in FIG. 4.

FIG. 4 illustrates the welding helmet 1 according to one embodiment of the present application. This welding helmet 1 is equipped with the HUD-type auto-darkening filter 10 according to the present application. Further as shown in FIG. 5, the welding helmet 1 comprises a helmet housing 40, the HUD-type auto-darkening filter 10 installed at a front part of the helmet housing 40, and a headband structure 60. The headband structure 60 is used to be directly worn on the operator's head so as to secure the helmet housing 40 there in place. The front part of the helmet housing 40 is formed with a substantially rectangular opening 40a in which a support frame 50 is installed. The previously-cited HUD-type auto-darkening filter 10 is installed onto the support frame 50 such that after the support frame 50 is secured within the helmet housing 40 in place, the luminous side of the head-up display 10c of the auto-darkening filter 10 is oriented upwards and obliquely, as shown in FIG. 4.

The knob 30 is arranged on the helmet housing 40 to adjust the auto-darkening filter 10 such that it is convenient for the operator to directly and manually manipulate the knob 30 to adjust the parameters. A transparent protective sheet 20' is arranged at the opening 40a of the helmet housing 40 such that the sheet is in front of the auto-darkening filter 10. It should be understood that the transparent protective sheet 20' can be the same as the glass sheet 20 shown by FIGS. 1 and 2. The transparent protective sheet 20' is spaced from the auto-darkening filter 10, especially the liquid crystal filter lens module 10a, by a distance and at the same time the head-up display 10c is arranged obliquely such that as the underneath head-up display 10c is activated, a virtual image generated via the transparent protective sheet 20' can be exactly watched by the operator's eyes.

Figure 6:
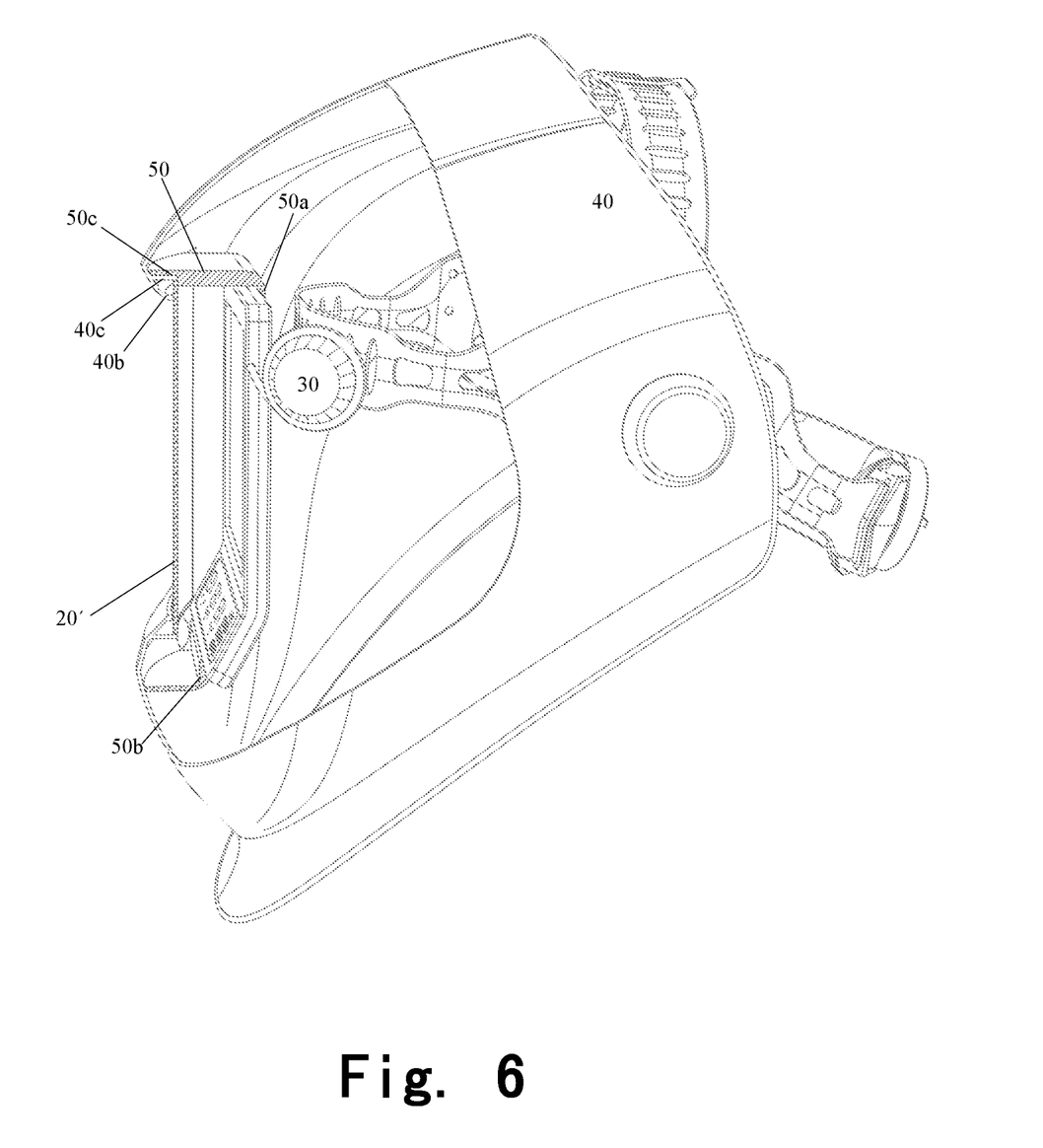
FIG. 6 is a partially sectional and perspective view schematically illustrating the welding helmet shown by FIG. 4.

How to install the auto-darkening filter 10 in the helmet housing 40 will be explained below. As shown in FIGS. 5 and 6, the support frame 50 is generally in the form of a rectangular frame. The support frame is provided with a flange 50a which extends inwards at a side of the frame adjacent to the operator's head. The flange 50a has a bent shape which conforms to the body of the auto-darkening filter 10 and its head-up display 10c, such that the body of the auto-darkening filter 10 and its head-up display 10c can be fitted against the flange 50a. A support lip 50b is provided at the bottom of the support frame 50. The support lip 50b is used to abut the head-up display 10c upwards such that the head-up display 10c is prevented from falling out of the support frame 50. It should be understood that the auto-darkening filter 10 can be secured onto the support frame 50 via any suitable manner such as bonding, screw fastening, crimping, snapping or the like, known by the skilled person in the art.

Two flanges 40c and 40b are formed around the opening 40a of the helmet housing 40. The support frame 50 is fitted onto the flange 40c via a front flange 50c. Then, the protective sheet 20' can be placed between the flange 40b and the support frame 50 in a front and back direction. The protective sheet 20' can be secured by a clamping force between the flange 40b and the support frame 50. It should be understood that the protective sheet 20' can be secured between the support frame 50 and the helmet housing 40 in the opening 40a of the helmet housing 40 via any suitable manner such as bonding, screw fastening, crimping, snapping or the like.

When it is desirable to use the welding helmet 1 according to the present application, the operator can first wear the welding helmet 1 on his/her head, and then manipulates the knob 30. Through the head-up display 10c, the operating parameters can be manifested as virtual images in front of the operator's eyes. In this way, taking off/wearing the helmet as required in the prior art is not necessary. After re-adjusting the operating parameters, the operator can directly carry out a welding operation, which can reduce his/her labour strength and improve his/her work efficiency. Further, with respect to the welding helmet 1, according to the present application, the operator can directly adjust or observe the operating parameters of the auto-darkening filter without taking off the welding helmet. Therefore, one's eyes will not have to adapt to bright or dark environmental light change. Possible discomfort of the operator is relieved and his/her eyes can be further reliably protected.

Although in the illustrated embodiment the head-up display 10c is integrated with the body carrying with the liquid crystal filter lens module 10a and the solar battery module 10b, it is understood by the skilled person in the art that the head-up display 10c can be designed separately from the body of the auto-darkening filter 10. For example, in an alternative embodiment, the head-up display 10c and the body of the auto-darkening filter 10 can be manufactured separately from each other; then, the head-up display is connected to the body of the auto-darkening filter 10 and the knob 30 via data cables respectively. In this way, it will be more convenient to select a location where the head-up display 10c should be arranged in the helmet housing 40. For example, the head-up display can be chosen to be arranged at a location where it facilitates generation of the virtual image. Furthermore, in an alternative embodiment, the head-up display 10c can be arranged at the left or right or even top of the body of the auto-darkening filter 10 as long as the head-up display 10c arranged obliquely towards the protective sheet 20' can be used to generate a virtual image which can be observed by the operator.

Further, as already cited, the transparent protective sheet 20' of the helmet 1 can be the glass sheet 20 shown by FIGS. 1 and 2. However, because the spattering matters caused by the welding operation will directly contact the protective sheet 20' or the glass sheet 20 to scratch their surface such that the generated virtual image is not clear enough to affect observation of the operating parameters, the protective sheet 20' or the glass sheet 20 can be removably installed on the helmet housing 40. For instance, in an alternative embodiment, several detachable catch structures can be provided around the opening 40a on the helmet housing 40, by which catch structures the protective sheet 20' or the glass sheet 20 can be detachably locked onto the helmet housing 40. In this way, when the protective sheet 20' or the glass sheet 20 is over-scratched to affect the observation, they can be replaced by new ones. For instance again, the protective sheet 20' or the glass sheet 20 and the helmet housing 40 can be perforated respectively such that screws can be used to secure the protective sheet 20' or the glass sheet 20 on the helmet housing 40. If needed, the protective sheet 20' or the glass sheet 20 can be replaced by a new one after the screws are loosened. In brief, any detachable fixation device known by the skilled person in the art can be applied between the protective sheet 20' or the glass sheet 20 and the helmet housing 40.

Furthermore, the protective sheet 20' can be semitransparent or dark colored to ensure that clearer imaging can be made. Furthermore, the protective sheet 20' can be a commonly-used protective sheet of the known auto-darkening welding helmet, to whose outer surface a transmitting and reflective film is affixed as a reflective screen for the head-up display. In this way, after a period of time, when the spattering matters render the generated virtual image not clear enough, clearer imaging can be ensured only by tearing the old film and affixing a new one.

In contrast to the known welding helmet, the operator can directly wear the inventive welding helmet on his/her head to activate the head-up display and to image the welding helmet's operating parameters in front of the protective sheet. In this way, those parameters can be adjusted by manually manipulating the knob. After adjustment, the operator can directly carry out a welding operation with welding-arc ignition by deactivating the head-up display. Further, in order to adjust the operating parameters or the welding modes during the welding operation, the operator can enable the auto-darkening filter to become in a transparent state and then activate the head-up display again. After the operating parameters are adjusted, the operator can carry out the welding operation again. It can be seen that since the welding helmet is equipped with the HUD-type auto-darkening filter according to the present application, it is unnecessary for the operator to take off the helmet, adjust the parameters and wear it again as required in the prior art. Rather, the operator can adjust the relevant operating parameters with wearing the helmet on his/her head. The convenience of the operator's work is improved and his/her eyes will not feel any discomfort caused by rapid change of ambient light. Therefore, the operator's work efficiency can be enhanced. Moreover, using the inventive welding helmet, the operator can carry out the welding operation especially in dark environmental condition because the imaging of the head-up display will be much clearer in this case.

Although the specific embodiments of the present application have been explained in details, they are given for illustrative purposes only and cannot be thought to constitute any limitation to the present application. Any modification, change or combination to the embodiments described here which can be made by those skilled in the art after reading the present specification without departing from the spirit of the present application fall within the scope of the present application.

The invention claimed is:

1. A welding helmet comprising:
a helmet housing;
a headband structure for securing the helmet housing;
an auto-darkening filter secured in the helmet housing; and
a light-permeable protective sheet installed in the helmet housing in front of the auto-darkening filter,
wherein the auto-darkening filter comprises:
a body;
a filter lens module installed in the body of the auto-darkening filter, the filter lens module configured to provide automatic light filtering; and
a head-up display installed aside the filter lens module in the body of the auto-darkening filter, arranged obliquely relative to the filter lens module and the protective sheet, and facing toward the protective sheet, the head-up display configured to luminously reveal operating parameters of the filter lens module such that, when the filter lens module is in a transparent state, the luminously revealed operating parameters of the filter lens module are (i) projected obliquely relative to the filter lens module by the head-up display such that one part of a light ray emitted by the head-up display transmits through the light-permeable protective sheet and (ii) reflected obliquely relative to the protective sheet, via the protective sheet, through the filter lens module for visibility by an operator of the welding helmet such that another part of the emitted light ray is reflected by the light-permeable protective sheet and through the filter lens module to provide a virtual image of the luminously revealed operating parameters a given distance from the light-permeable protective sheet.

2. The welding helmet as cited in claim 1, wherein the protective sheet is spaced from the body of the auto-darkening filter such that the virtual image of the luminously revealed operating parameters of the filter lens module generated via the protective sheet is visible to the operator.

3. The welding helmet as cited in claim 1, wherein the head-up display is configured to luminously reveal each of the operating parameters in a reversed manner.

4. The welding helmet as cited in claim 1, wherein the head-up display is arranged obliquely relative to the protective sheet in the helmet housing.

5. The welding helmet as cited in claim 4, wherein the head-up display is arranged at a bottom of the body of the auto-darkening filter in the helmet housing.

6. The welding helmet as cited in claim 1, wherein the head-up display comprises a monochromatic or color display screen.

7. The welding helmet as cited in claim 1, wherein an adjustment knob is installed on the helmet housing of the welding helmet and is connected to the auto-darkening filter such that the adjustment knob can be used to adjust the operating parameters.

8. The welding helmet as cited in claim 7, wherein adjustment of the operating parameters comprises adjustment of SHADE, which can be adjusted between 9 and 13 levels; adjustment of SENSITIVITY, which can be adjusted between 0 and 10 levels; adjustment of DELAY TIME, which can be adjusted between 0 and 10 levels; and adjustment of welding mode, which can be switched between WELD, GRIND and CUTTING.

9. The welding helmet as cited in claim 1, wherein the protective sheet is transparent or semitransparent.

10. The welding helmet as cited in claim 1, wherein the protective sheet is detachably installed in the helmet housing.

11. The welding helmet as cited in claim 1, wherein the provided virtual image is an enlarged virtual image of the luminously revealed operating parameters.

12. The welding helmet as cited in claim 11, wherein the enlarged virtual image is projected externally of the welding helmet.

13. The welding helmet as cited in claim 1, wherein the parameters are reflected upwards toward the filter lens module.

14. The welding helmet as cited in claim 1, wherein head-up display is installed below the filter lens module.

15. The welding helmet as cited in claim 1, further comprising a support frame configured to house the body, the filter lens module, and the head-up display.

16. The welding helmet as cited in claim 15, wherein the support frame comprises:
a flange that includes a bent shape configured to support the filter lens module; and
a support lip configured to abut the head-up display upwards.

17. The welding helmet as cited in claim 15, wherein the support frame is secured to the helmet housing.

* * * * *